United States Patent [19]

Suckewer et al.

[11] Patent Number: 4,979,203
[45] Date of Patent: Dec. 18, 1990

[54] X-RAY LASER MICROSCOPE APPARATUS

[75] Inventors: Szymon Suckewer, Princeton; Darrell S. DiCicco, Plainsboro, both of N.J.; Joseph G. Hirschberg, Coral Gables, Fla.; Lewis D. Meixler, East Windsor, N.J.; Robert Sathre, Princeton, N.J.; Charles H. Skinner, Lawrenceville, N.J.

[73] Assignee: Princeton X-Ray Laser, Monmouth Junction, N.J.

[21] Appl. No.: 369,206

[22] Filed: Jun. 19, 1989

[51] Int. Cl.⁵ ............................................. G21K 7/00
[52] U.S. Cl. ....................................... 378/206; 378/43; 378/63
[58] Field of Search ................... 378/206, 43, 205, 63, 378/208, 68; 350/534, 571

[56] References Cited

U.S. PATENT DOCUMENTS

| | | |
|---|---|---|
| 2,557,662 | 6/1951 | Kirkpatrick . |
| 2,559,972 | 7/1951 | Kirkpatrick . |
| 2,617,942 | 11/1952 | McLachlan, Jr. et al. . |
| 2,754,425 | 7/1956 | Froemel . |
| 2,759,106 | 8/1956 | Wolter . |
| 2,877,353 | 3/1959 | Newberry . |
| 2,939,954 | 6/1960 | Ong . |
| 3,143,651 | 8/1964 | Giacconi . |
| 3,407,296 | 10/1968 | Armstrong . |
| 3,705,305 | 12/1972 | Fischer ............................. 378/206 |
| 3,743,845 | 7/1973 | Rabodzei et al. . |
| 3,818,233 | 6/1974 | Rabodzei et al. . |
| 3,846,632 | 11/1974 | Rabodzei et al. . |
| 3,860,819 | 1/1975 | Rabodzei et al. . |
| 4,253,154 | 2/1981 | Russ et al. . |
| 4,317,036 | 2/1982 | Wang . |
| 4,538,291 | 8/1985 | Iwamatsu . |
| 4,562,583 | 12/1985 | Hoover et al. . |
| 4,596,030 | 6/1986 | Herziger et al. . |
| 4,704,718 | 11/1987 | Szymon . |
| 4,771,430 | 9/1988 | Suckewer et al. . |
| 4,799,246 | 1/1989 | Fischer ............................. 378/206 |

OTHER PUBLICATIONS

M. Rousseau, Spectrophotometrie de Fluorescence en Microscopie, Bull. Microscopie Appl. 7, 92–94 (1957).
T. Caspersson, G. Lomakka, and R. Rigler, Jr., Regiestrierender Sedundarfluoreszenz Verschiedene Zellsubstanzen, Act. Histochem Suppl. 6, 135–153 (1965).
P. Daudel, M. Croisy–Delcey, C. Alson–Verduras, M. Duquesne, P. Jacquignon, P. Markovits, et al., P. Vigny, Etude par Fluorescence.
d'Acides Nucleiques Extraits de Cellules en Culture Traitees par le Methyl Benzo(a) Anthracene, Comptes Rend. Acad. Sci. Paris, 278, 2249–2252 (1974).
S. Suckewer et al., Phys. Rev. Lett 57, 1004 (1986).
B. Chance, and B. Thorell, Localization and Kinetics of Reduced Pyridine Nucleotides in Living Cells by Mi- (List continued on next page.)

Primary Examiner—Carolyn E. Fields
Assistant Examiner—David P. Porte
Attorney, Agent, or Firm—Mathews, Woodbridge & Collins

[57] ABSTRACT

A microscope consisting of an x-ray contact microscope and an optical microscope. The optical, phase contrast, microscope is used to align a target with respect to a source of soft x-rays. The source of soft x-rays preferably comprises an x-ray laser but could comprise a synchrotron or other pulse source of x-rays. Transparent resist material is used to support the target. The optical microscope is located on the opposite side of the transparent resist material from the target and is employed to align the target with respect to the anticipated soft x-ray laser beam. After alignment with the use of the optical microscope, the target is exposed to the soft x-ray laser beam. The x-ray sensitive transparent resist material whose chemical bonds are altered by the x-ray beam passing through the target material, is then developed to produce a shadow image of the target.

15 Claims, 5 Drawing Sheets

OTHER PUBLICATIONS crospectrofluorometry, Jour. Biol. Chem. 234, 3044–3050 (1959).

R. A. Olson, Rapid Scanning Microspectrofluorometer, Rev. Sci. Instr. 31, 844–849 (1960).

B. Thorell, E. Kohen, and C. Kohen, Metabolic Rates and Intercellular Transfer of Molecules in Cultures of Human Glia and Glioma Cells, Med. Biol. (Helsinki), 56, 386–392 (1978).

G. H. I. Sloane, and C. N. Loesser, Spectroscopic Analysis of Carcinogenic Hydrocarbons in Biologic Interactions in Vivo and in Vitro, Cancer Res. 23, 1555–1556 (1963).

J. M. Salmon, E. Kohen, C. Viallet and F. Zajdela, A Preliminary Microspectrofluorometric Study of NAD(P)H Reduction in Dibenzo(a,e) Fluoranthrene--Treated Single Living Cells, Histochem 47, 291–302 (1976).

B. Thorell, Flow-Cytometric Monitoring of Intracellular Flavins Simultaneously with NAD(P)H Levels, Cytometry 4, 61–65 (1983).

A High Resolution Grating Microspectrofluorometer with Topographic Option for Studies in Living Cells, J. G. Hirschberg, et al., A.C.S. Symposium Series No. 102 Multichannel Image Detectors, Yair Talmi, Editor. American Chemical Society, 1979.

S. Suckewer et al., Phys. Rev. Lett. 55, 1753 (1985).

S. Suckewer et al., Physique, Supplement 10, vol. 47 C6–23 (1986).

X-RAY LASER MICROSCOPE APPARATUS

GOVERNMENT LICENSE RIGHTS

This invention was made with government support under Contract No. De-FG02-86ER13609 awarded by the Department of Energy. The Government has certain rights in this invention.

BACKGROUND OF THE INVENTION

1. Field of the Invention

The invention relates to a method and apparatus for performing contact x-ray microscopy using an optical, phase contrast microscope for inspecting and aligning a target prior to exposing the target to a source of soft x-rays.

2. Description of Related Art

Numerous efforts have been made in the past to examine small objects using x-rays. Early efforts have always encountered problems when making observations with x-rays especially for small objects which were especially difficult to cope with when living media was the target.

Perhaps the most relevant prior reference is U.S. Pat. No. 2,877,353 entitled X-RAY MICROSCOPE. It describes what is known as an x-ray shadow wherein a target is bombarded by x-rays and its shadow is recorded on an x-ray sensitive medium. The x-ray sensitive medium could be a television screen or a film or the like. U.S. Pat. No. 2,939,954 entitled X-RAY SHADOW MICROSCOPE also discloses another early effort to capture x-ray images of targets.

The following U.S. Pat. Nos. describe efforts to use television in the context of x-ray microscopes: 3,818,233; 3,743,845; 3,846,632 and 3,860,819. U.S. Pat. No. 3,818,233 also suggests the possibility of using an optical device in combination with an x-ray television microscope.

The following U.S. Pat. Nos. describe prior x-ray microscopes of more general relevance: 2,617,942; 2,754,425; 3,079,501; 3,143,651; and 4,317,036.

It is also possible to have the reverse of a microscope, namely a telescope. See, for example, U.S. Pat. No. 4,562,583 entitled SPECTRAL SLICING X-RAY TELESCOPE WITH VARIABLE MAGNIFICATION.

Sources of x-rays which might be employed for microscopes or for other purposes are described in U.S. Pat. Nos. 4,538,291 and 4,596,030 as well as in other prior art sources.

Descriptions of other devices for producing soft x-ray beams may be found, for example, in U.S. Pat. Nos. 4,704,718 entitled APPARATUS AND METHOD FOR GENERATING SOFT X-RAY LASING ACTION IN A CONFINED PLASMA COLUMN THROUGH THE USE OF A PICOSECOND LASER and U.S. Pat. No. 4,771,430 entitled ENHANCEMENT OF SOFT X-RAY LASING ACTION WITH THIN BLADE RADIATORS. While the use of soft x-ray lasers in the context of x-ray microscopy has been speculated about over the years, there is no known discussion of the use of such device in the specific apparatus and combination taught in this disclosure.

The following U.S. Pat. Nos. are of possible relevance in that they relate to x-ray imaging: 2,557,662; 2,559,972; 2,759,106; 3,407,296 and 4,253,154.

In addition to the foregoing patents, the following literature references may also be relevant:

1. M. Rousseau, Spectrophotometrie de Fluorescence en Microscopie, Bull. Microscopie Appl. 7, 92–94 (1957).
2. B. Chance, and B. Thorell, Localization and Kinetics of Reduced Pyridine Nucleotides in Living Cells by Microspectrofluorometry, Jour. Biol. Chem. 234, 3044–3050 (1959).
3. R. A. Olson, Rapid Scanning Microspectrofluorometer, Rev. Sci. Instr. 31, 844–849 (1960).
4. T. Caspersson, G. Lomakka, and R. Rigler, Jr., Regiestrierender Sedundarfluoreszenz Verschiedene Zellsubstanzen, Act. Histochem. Suppl. 6, 135–153 (1965).
5. B. Thorell, E. Kohen, and C. Kohen, Metabolic Rates and Intercellular Transfer of Molecules in Cultures of Human Glia and Glioma Cells, Med. Biol. (Helsinki) 56, 386–392 (1978).
6. G. H. I. Sloane, and C. N. Loesser, Spectroscopic Analysis of Carcinogenic Hydrocarbons in Biologic Interactions in vivo and in Vitro, Cancer Res. 23, 1555–1556 (1963).
7. P. Daudel, M. Croisy-Delcey, C. Alonso-Verduras, M. Duquesne, P. Jacquignon, P. Markovits, et al. P. Vigny, Etude par Fluorescence d'Acides Nucleiques Extraits de Cellules en Culture Traitees par le Methyl Benzo(a)anthracene, Comptes Rend. Acad. Sci. Paris 278, 2249–2252 (1974).
8. J. M. Salmon, E. Kohen, C. Viallet and F. Zajdela, A Preliminary Microscptrofluorometric Study of NAD(P)H Reduction i Dibenzo (a,e) Fluoranthrene-Treated Single Living Cells, Histochem 47, 291–302 (1976).
9. B. Thorell, Flow-Cytometric Monitoring of Intracellular Flavins Simultaneously with NAD(P)H Levels, Cytometry 4, 61–65 (1983).
10. A High Resolution Grating Microspectrofluorometer with Topographic Option for Studies in Living Cells, J. G. Hirschberg, et al., A.C.S. SYMPOSIUM SERIES No. 102 Multichannel Image Detectors, Yair Talmi, Editor. American Chemical Society, 1979.
11. S. Suckewer et al., Phys. Rev. Lett. 55, 1753 (1985).
12. S. Suckewer et al., Phys. Rev. Lett. 57, 1004 (1986).
13. S. Suckewer et al., physique, Supplement 10, Vol. 47 C6-23 (1986).

In the study of the functions of the living cell, one of the most successful approaches has been the use of monolayer cultures of cells which exhibit the fluorescence of naturally occurring coenzymes produced by the life processes of the cell especially in NADH and flavo proteins. Descriptions of the foregoing can be found in literature references numbered 1 through 5 above. Another highly successful application of fluorescence is in the detection and determination of the fate of foreign materials in a cell, known as xenobiotics, such as carcinogens and their poisons. Further discussions of the foregoing are findable in literature references number 6 through 9 referred to above. Both applications are made possible by the remarkable sensitivity of the fluorescence method where as little as one part in a quadrillionth of a mole can be detected.

In the prior art, the resolution available was generally limited to about 250 nm when visible light wavelengths were employed. In many experiments, however, especially where the mechanism of a cell's defense against xenobiotics is investigated, fluorescence was found to spread throughout the cell a few seconds after injection. The exact mechanism of fluorescent spreading remains obscure due to the limitation of the available resolution. Attempts have been made to obtain increased information by circling the injected cell or cells with a diamond, and later using an electron microscope. Unfortunately, this technique suffers from the problem that the cells must be desiccated and then shadowed with evaporated metal before placing them in the electron microscope. All time-resolution is lost by this process, and the cellular structure is, of course, altered thereby.

References number 11-13 above relate to sources of soft x-ray laser beams which might be advantageously employed with the present invention. The foregoing references further discuss the soft x-ray laser devices found in U.S. Pat. Nos. 4,704,718 and 4,771,430 previously described.

A useful overview of the state of the art of x-ray microscopes can be found in an article entitled "Soft-x-ray Microscopes", Physics Today, August 1985, pages 22-32.

The use of photoresists as applied to x-ray microscopes is discussed in an article entitled "Specimen Replication for Electron Microscopy Using X-Rays and X-Ray Resist", Journal of Applied Physics, Vol. 47, No. 3, March 1976, pages 1192-1193.

The measurement of calcium using soft x-rays is discussed in an article entitled "Absorption Microanalysis with a Scanning Soft X-Ray Microscope: Mapping the Distribution of Calcium in Bone" by J. M. Kennedy et al., Journal of Microscopy, Vol. 138, June 1985 pages 321-328.

Lastly, two additional useful background articles relating to the state of the art of high resolution microscopes include "Scanning X-Ray Microscope with 75-nm Resolution", by H. Rarback, et al., Rev. Sci. Instrum. 59(1), January 1988 pages 52-59 and "Some Experiences with X-Ray and Proton Microscopes", by Paul Horowitz, New York Academy of Sciences, 1978, pages 203-222.

Insofar as understood none of the forementioned references describes an apparatus or method for x-ray microscopy with an effective way to align a target, especially a target comprising living cells with an optical microscope prior to exposure by a soft x-ray beam.

SUMMARY OF THE INVENTION

Briefly described the invention comprises an x-ray contact microscope and an optical microscope. A method and apparatus is taught for aligning a target with respect to a source of soft x-rays prior to exposure. The target is positioned on top of transparent resist material so that it is visible from above and below. An inverted, Leitz Diavert, phase contrast, type microscope, can inspect and align the target from below prior to exposure. Once the target is aligned it is exposed to a soft x-ray laser beam which produces an image on the resist material. The resist material is subsequently developed and the image examined.

Soft, as opposed to hard, x-rays do not travel well in air. Accordingly it is necessary for the evacuated x-ray chamber to come right down to and almost on top of the target itself. This makes it extremely difficult to optically inspect the target since the soft x-ray equipment is right above it. By employing a transparent resist material and aligning and inspecting the target from the side opposite the x-ray source, it is possible to overcome many prior problems associated with the prior art.

These and other features of the invention will be more fully understood by reference to the following drawings:

DETAILED DESCRIPTION OF THE INVENTION

During the course of this description like numbers will be used to illustrate like elements according to the different views which illustrate the invention.

Figure 1:
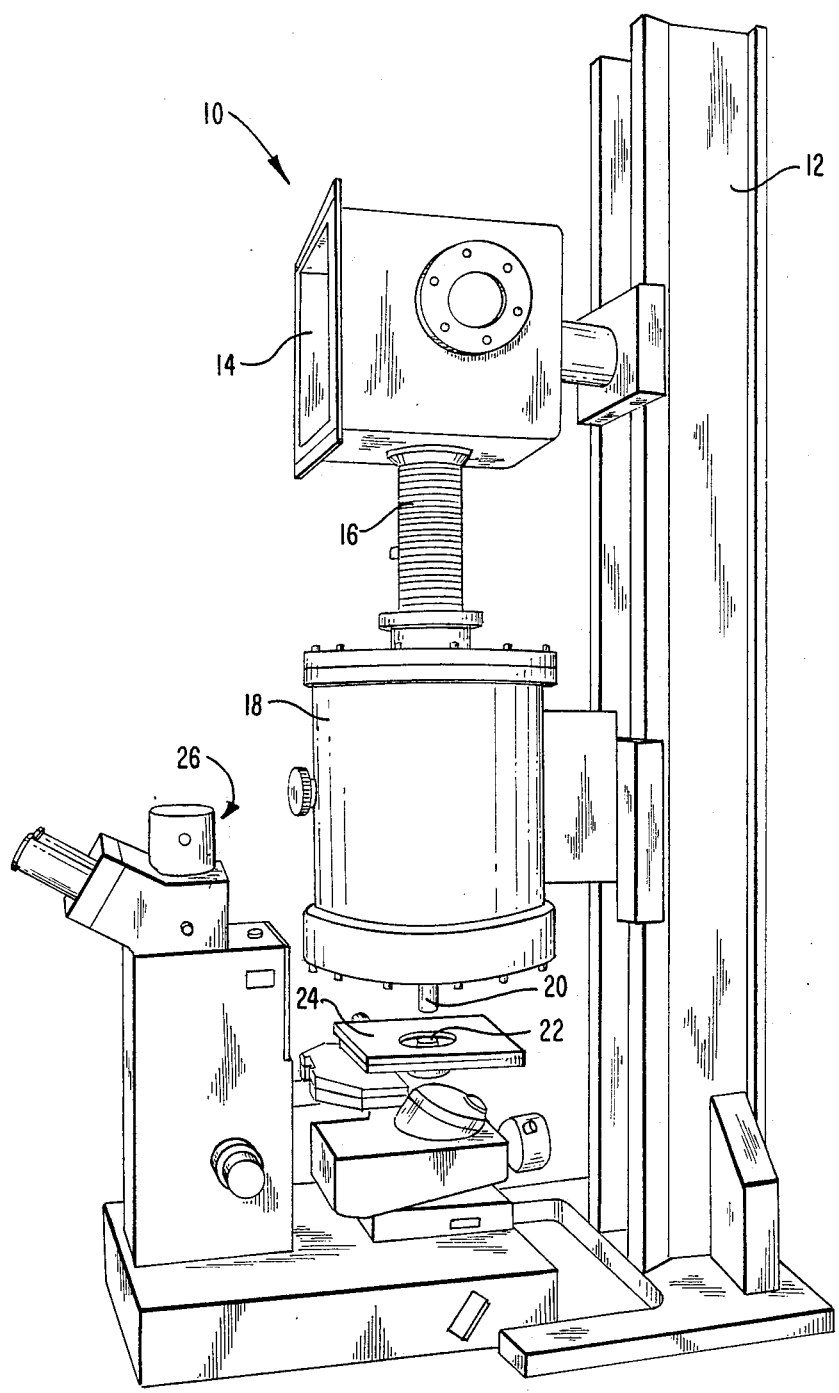
FIG. 1 is an exterior elevational view of the x-ray laser microscope invention according to the preferred embodiment thereof.

The exterior vertical view of the preferred embodiment 10 is illustrated in FIG. 1. A stand 12 supports a chamber 14 which includes a 45° multilayered mirror 13 for directing a beam 30, shown in FIG. 2, downward from an x-ray source 200. A soft x-ray beam 30 enters into mirror chamber 14, is turned 90° by multilayer mirror 13, and travels through flexible connection 16 and vacuum tight enclosure 32, shown in FIG. 2, and emerges through a 0.1 micron thick silicon nitride ($Si_3N_4$) window 20. Object cells 22 supported by stage 24 are exposed to the soft x-ray beam 30 that emerges from window 20. An inverted microscope 26 positions the object cells 22 with respect to the anticipated soft x-ray beam 30 so that the two are in proper alignment prior to exposure.

Figure 2:
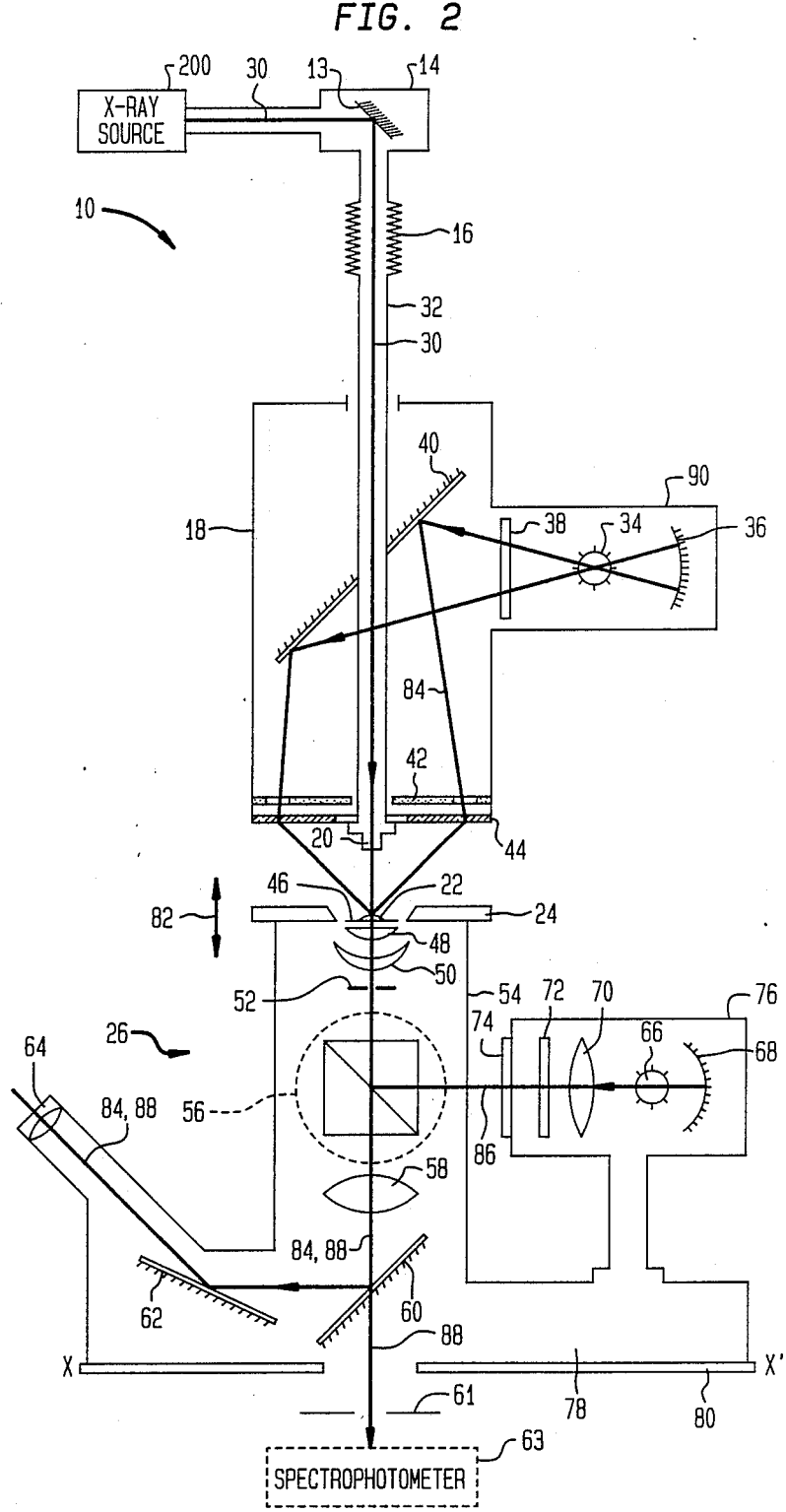
FIG. 2 is a schematic cross-sectional view of the preferred embodiment shown in FIG. 1.

The schematic details of the x-ray laser microscope invention 10 are seen in further detail in FIG. 2. A vacuum tight tube 32 forming an evacuated enclosure for beam 30 surrounds the soft x-ray beam 30 as it passes through the flexible bellows connection 16 from the upper mirror chamber 18. A tungsten-halogen light source 34 is focused by curved mirror 36 through a red filter 38 onto a 45° mirror 40 which in turn reflects the beam 84 through annular aperture 42 onto Fresnel condenser lens 44 which focuses the beam onto object cells 22. Condenser lens 44 is a focusing element that assures that light 84 from red light source 34 is focused on the object cells 22 and fills phase ring 52 with light. The light source 34 is housed in red light lamphouse 90. Object cells 22 have previously been cultured on a thin (less than 1 micrometer) film of transparent x-ray resist 46 deposited on a standard $50 \times 60 \times 0.14$ millimeter microcover glass. Condenser 44 and window 20 are positioned so that there is enough room (approximately 80 millimeters) above the object cells 22 for micromanipulation (e.g. injection) while at the same time, the microscope 26 can be used with a 100 X phase objective lens 50. This is important for injections. The dimensions of the annular aperture 44 and the condenser lens 44 are such that the phase ring 52 is just filled with light.

The soft x-ray laser beam 30 contacts object cells 22 and resist 46 but is generally too weak to pass much further. However, red light beam 84 passes through lens 48 before passing through the high power 100X phase objective lens 50. Beam 84 then continues through phase ring 52, Ploem Block 56 another lens 58 and onto a beam splitter 60. A portion of the beam 84 may continue into a spectrophotometer 63 while another portion is deflected off of mirror 62 and into the eyepiece 64 (or camera) of the inverted microscope 26. Base plate 80 supports the bottom of the apparatus 10 along with support stand 12 which also supports the Leitz Diavert base 78. The Leitz Diavert base 78 was manufactured by Ernst Leitz Wetzlar GmBh, D-6330 Wetzlar, West Germany and sold and distributed by the Kremer Scientific Corporation of Yonkers, New York. An ultraviolet light lamphouse 76 provides ultraviolet illumination for inspection of the cells 22. A mercury light source 66 is focused by curved mirror 68 through lens 70 and filters 72 and 74 onto the Ploem Block 56 as a beam 86 of ultraviolet light. The red light beam 84 is useful for visual inspections whereas the ultraviolet light beam 86 is initially reflected upward.

The ultraviolet light beam 86 causes the cells 22 to fluoresce. Light from the visible end of the spectrum is emitted from the cells 22, and passes back down through Ploem Block 56 as a beam of visible light 88 and through the dichroic surface 60 and through entrance slit 61 to the spectrophotometer 63 for inspection of fluorescent activity. Two-way arrow 82 indicates that the stage 24 carrying resist 46 and object cells 22 may be moved up and down with respect to condenser 42 and window 20.

Figure 3:
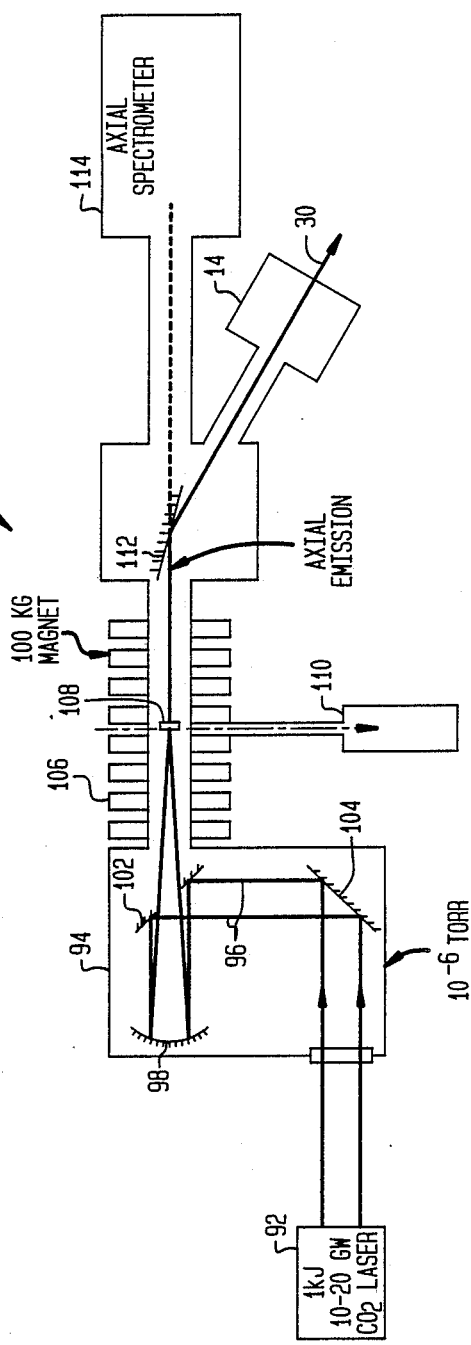
FIG. 3 illustrates the source of the soft x-ray laser beam employed with the preferred embodiment.

FIG. 3 is a schematic of the x-ray laser source 200 as configured for use with the x-ray laser microscope 10. The x-ray laser source 200 is typical of a preferred source of x-rays but is not meant to suggest that it is the only possible source. Other sources are also possible. A 1KJ, 10–20GW, $CO_2$ laser 92 produces a beam 96 which enters enclosure 94 having a vacuum at about $10^{-6}$ Torr. Beam 96 reflects off mirror 104, mirror aperture 102 and is reflected by curved mirror 98 respectively and is focused onto target 108. The interaction of the beam 96 with the target 108 results in the formation of a highly ionized gas referred to as a plasma. Atomic processes associated with the return of the plasma to thermal equilibrium result in the generation of a population inversion and the emission of a beam 30 of x-rays. A 100KG magnet 106 confines the plasma. Radial emission from the impact of the beam 96 on target 108 is monitored by radial spectrometer 110. The beam then impinges upon mirror 112 such that a portion 30 enters the x-ray laser microscope 10 through the box 14 which contains multilayered mirror 13 which directs the beam 30 downward in a vertical direction to the microscope 10. The x-ray beam 30 is preferably in the range of 1 Angstrom to 250 Angstroms or 0.1 nm to 25 nm in wavelength.

Figure 4:
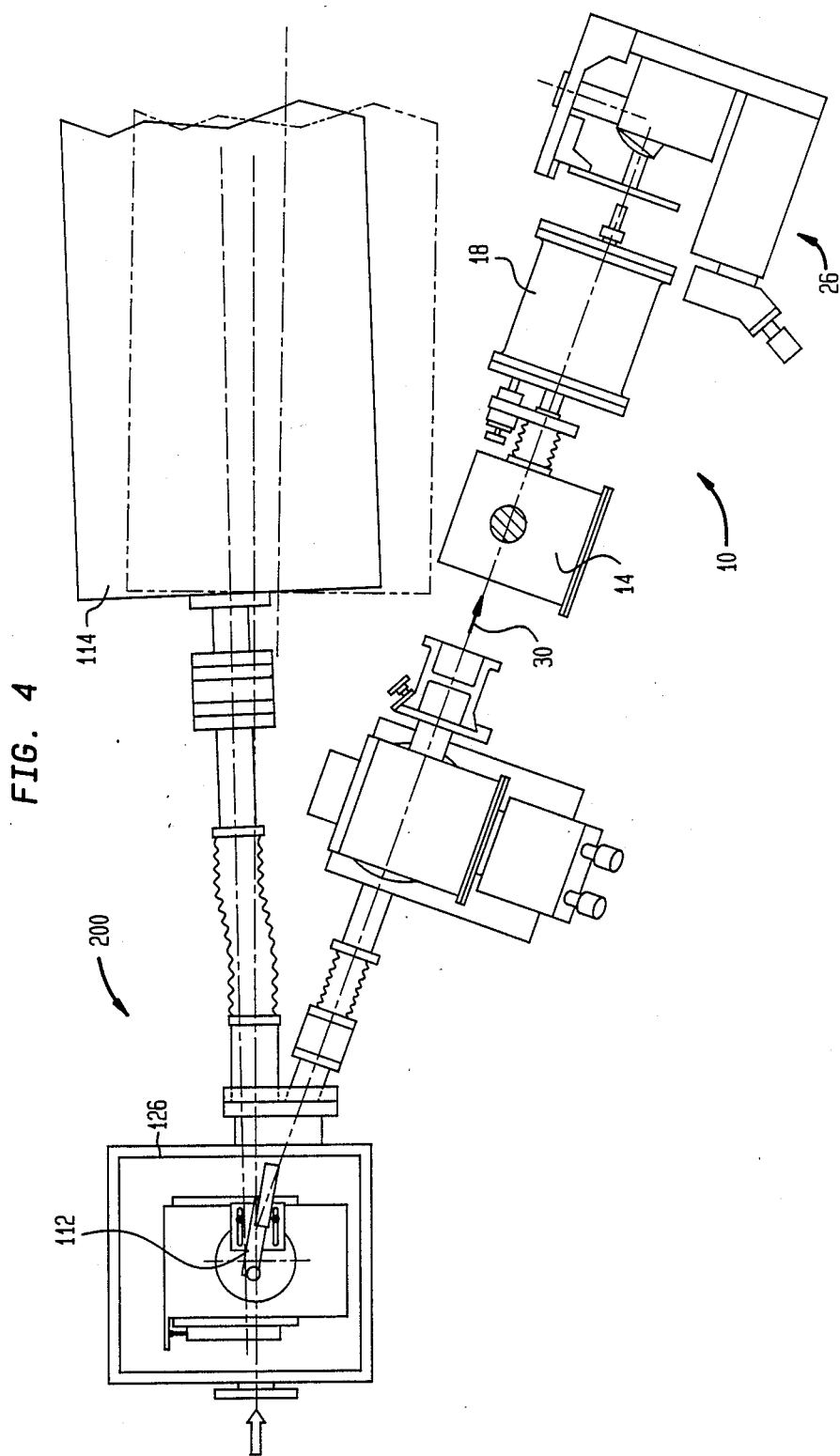
FIG. 4 illustrates the downstream portion of the invention.
Figure 5:
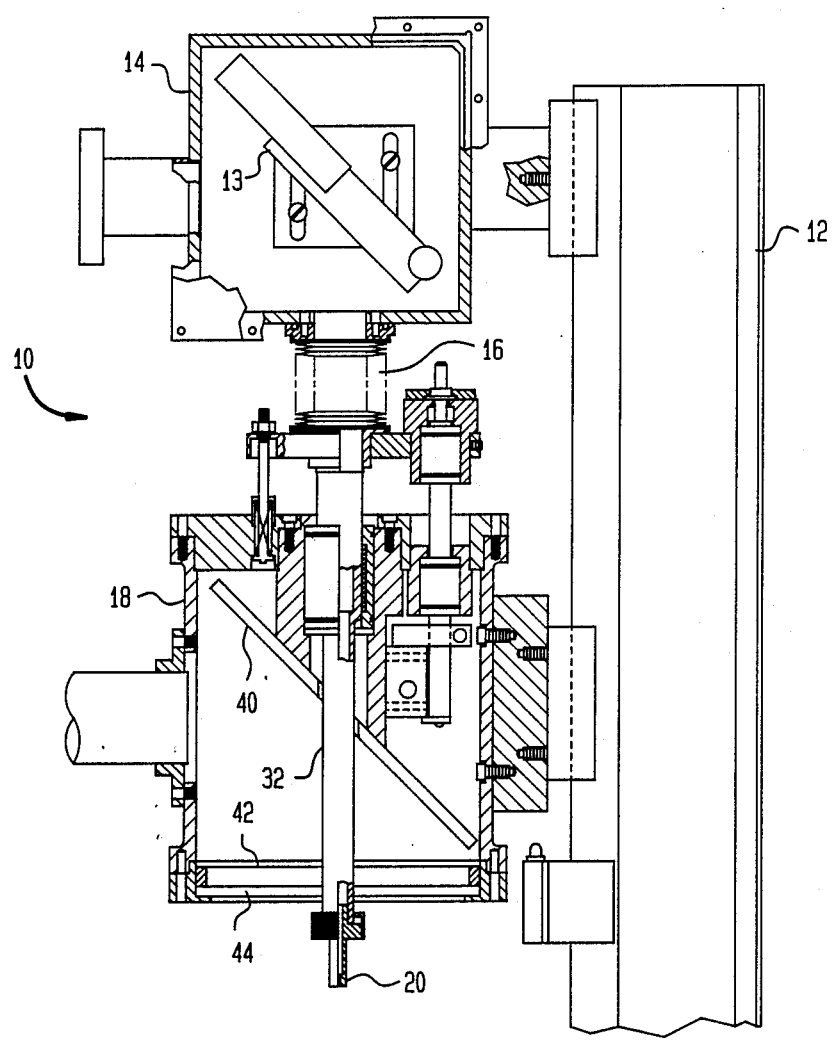
FIG. 5 is a detailed mechanical cross-sectional view of the invention.
Figure 6:
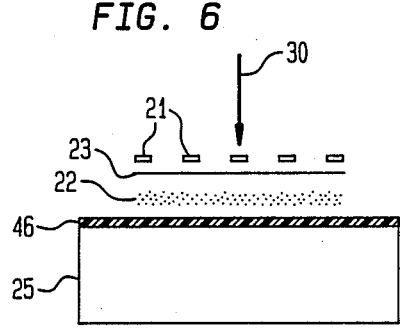
FIG. 6 is a cross-sectional detail of a section of photoresist showing the manner in which the specimens are prepared for exposure to soft x-rays.

FIG. 4 illustrates the exterior of the downstream portion of the invention as the beam 30 emerges from the source and passes into the x-ray laser microscope 10. FIG. 5 is a mechanical cross-sectional detail of the upper portion of the soft x-ray laser microscope according to the preferred embodiment.

The preferred photoresist 46 was PBS (polybutene-1-sulfone) which was more sensitive by a factor of three than copolymer resist. The PBS resist 46 was developed in methyl ethyl ketone (2 parts) and isopropanol (1 part) for 15 seconds. Initially, it was found to be difficult to remove the biological specimens 22 placed in contact with the resist 46 after x-ray exposure. This problem opened the way to the possibility of confusion because of the difficulty of distinguishing between the remnants 22 left on the resist 46 and the relief image formed in the resist 46. In order to avoid this problem, the biological specimens 22 were mounted on a 5 nm carbon film 23 supported on a TEM grid 21 as shown in FIG. 5. This was placed in contact with the resist 46 for x-ray exposure and could be easily removed and, if necessary, reused in later exposures.

Viewing of the developed image on the resist 46 was made with a scanning electron microscope (SEM). For example, a suspension of diatoms (silicified skeletons of planktonic algae) was placed on the photoresist 46 and left to dry. After exposure to the soft x-rays 30 the photoresist 46 was developed and viewed in a SEM. A resolution of 0.1 mn was apparent. Since diatoms are high contrast objects this technique would also be described as microlithography and illustrates the potential application of x-ray lasers to fields such as microelectronics.

The invention 10 has major advantages over the prior art. It allows, for example, for the injection of living cells by the method developed by E. Kohen as described in an article entitled METABOLIC RATES AND INTERCELLULAR TRANSFER OF MOLECULES AND CULTURES OF HUMAN GLIA AND GLIOMA CELLS, B. Thorell, E. Kohen, and C. Kohen, Med. Biol. (Helsinki) 56, 386–392 (1978). The injections may be either of the substrate and/or modifiers by which means the cells metabolic processes and reaction rates can be followed and measured. The reaction of the cell is measured for normal cells or cells altered by previous exposure to xenobiotics or other agents. The genetics of the cells reaction can then be easily studied. Also, in order to facilitate injections, the condenser lens 42 is provided with tungsten-halogen illumination from source 34. The aperture has a long working distance (approximately 80 mm) and a high numerical rating of approximately 1.38. The high numerical aperture rating of 1.38 refers to the Diavert microscope lens 48, 50 and 58. The higher the n.a. (numerical aperture), the higher the resolving limit of the microscope. An n.a. of 1.38 is the preferred value for embodiment 10. The fluorescent ultraviolet light source 66 helps to monitor the effect of injections. Finally, after the fluorescence is evaluated, the x-ray beam 30 can be used to determine the finer details of the cell.

For fluorescent excitation, a high pressure metal (e.g. mercury) arc source 66 is used which produces strong isolated spectral lines. Alternatively, a xenon arc can be used for a broader spectrum. The excitation radiation is sent through a dichroic beam-splitter 56 and then to the microscope objective lenses 48 and 50. Objective lenses 48 and 50 focus exciting light onto the cells 22. The resulting fluorescence in turn is carried back through the same objective lenses 48 and 50 and beam splitter 60 to the eyepiece or camera 64. The light will, in general, be shifted towards longer wavelengths, and will then be transmitted instead of reflected by the beam splitter 60. An image of the cell 22 is formed on a two-dimensionally variable slit 61 which provides a spectrometer slit for spectrophotometer 63.

During experiments, the selected cells 22 may be monitored for exogenous or endogenous fluorescence which is a factor of the metabolic rate. Injections may be used to modify the metabolic rate. Upper mirror chamber 18 mentioned above, provides just enough clearance for working space in order to perform injections.

When making x-ray exposures, a vacuum tube 20 is placed in general contact with the specimen 22 which has been cultured on the x-ray resist 46. The soft x-ray laser beam 30 is thus exactly centered over the cells 22 which have been modified and whose metabolic rate has been ascertained. If, for example, xenobiotics have been used, detoxification can be closely followed by metabolic rate changes, by localization of fluorescence, and by x-ray study.

Several sources of soft x-ray laser beams 30 can be employed. One technique for producing an appropriate soft x-ray laser beam is described in U.S. Pat. No. 4,771,430 entitled ENHANCEMENT OF SOFT X-RAY LASING ACTION WITH THIN BLADE RADIATORS. The invention can produce a laser beam 30 having the following parameters:

wavelength: 18.2 nm
beam power: 100 KW
beam energy: 1 to 3 millijoules
brightness: $5 \times 10^{19}$ photons/sec-mm$^2$-mrad$^2$-(0.01%BW)
pulse duration: 10 to 30 nsec.
divergence: 5 to 10 mrad.

Another acceptable system for developing x-ray laser beams 30 with wavelengths significantly below 10 nm (even down below 4 nm) is described in U.S. Pat. No. 4,704,718. According to that system the combination of a $CO_2$ laser with a powerful picosecond laser provides the proper lasing medium for short wavelength x-rays.

The techniques described above produce peak brightness that is 3 to 4 orders of magnitude greater than existing soft x-ray synchrotron sources which operate at wavelengths of 3 to 10 nm. In the future, it is expected that undulators can attain a brightness several orders of magnitude higher than present day synchrotrons. It is also expected that cavities developed for soft x-ray lasers will lead up to six orders of magnitude increase in laser brightness.

If a synchrotron source is used it may be pulsed at a high repetition rate with a pulse duration dictated by the length of an electron bunch (e.g. 6 MHz and 600 ps for the NSLS ring such as used at Brookhaven). Synchrotron sources and x-ray lasers can be viewed as complimentary sources of soft x-ray radiation. For instance, in applications where the duration of exposure is not important, synchrotrons may be the preferred source. Unfortunately, present and future synchrotrons and synchrotrons with undulators are not suitable for recording images of live cells. The reasons why are explained below.

In order to see live cells 22, a fluence of approximately 1mj/mm$^2$ is required over a period of time before damage to the cells 22 becomes apparent (on the order of magnitude equal to or less than 10 nanoseconds). These are values attainable by soft x-ray lasers such as described in U.S. Pat. Nos. 4,704,718 or 4,771,430. In comparison, the average power expected from synchrotrons with undulators is in milliwatts with corresponding exposure times in the order of seconds. Under such circumstances only the damaged remains of the cells 22 would be apparent in an image produced upon a resist material 46 if it came from such a synchrotron source. While the approximately 18.2 nm wavelength of the soft x-ray lasers described in U.S. Pat. Nos. 4,704,718 and 4,771,430 is, in general, less suitable for x-ray microscopy than synchrotron radiation at 3-4 nm, nevertheless for the study of vails or membranes of live cells (e.g. cancer cells) the 18.2 nm wavelength is quite appropriate. Moreover, it is anticipated that in the next few years soft x-ray lasers will be operational at wavelengths below 4.4 nm at the so called "water window" with a brightness of several orders of magnitude higher than present sources. The term "water window" defines a wavelength region in which there is relatively high contrast between water and biological material. Another advantage of soft x-ray laser sources such as described in U.S. Pat. Nos. 4,704,718 and 4,771,430 is that their size is relatively reasonable and their operational procedure is relatively simple. In summary, x-ray laser sources such as described in U.S. Pat. Nos. 4,704,718 and 4,771,430 produce acceptable high brightness, short pulses and have the potential in a few years of operating at wavelengths below 4.4 nm with a brightness of several orders of magnitude higher which lend themselves well to the study of living cells as well as chemical processes. In contrast, synchrotrons, due to their steady-state radiation and tunability over a relatively large range of energy, are especially appropriate for x-ray microscopy of non-living specimens. Accordingly, both sources of radiation for the x-ray beam 30 should be considered as complimentary for x-ray microscopy purposes.

The following are some applications of the soft x-ray laser microscope invention 10 described herein.

(a) Studies can be made of the location, i.e. mapping of calcium in the living cell. Deficiencies in calcium metabolism have been suspected in calcium diseases, especially cystic fibrosis. Some initial observations have already been made, using electron microscopy, but x-rays promise to extend these studies to living cells.

(b) The presence in living cells of metals, such as aluminum and magnesium, have been associated with certain diseases of the central nervous system, such as Alzheimer's disease and amyotrophic lateral sclerosis. The x-ray microscope invention 10 would allow detailed study of the presence of metals in the cell's organ, especially the Golgi apparatus, the endoplasmic reticulum or the lysozomics. The exact localization of metals in the cells is crucial to an understanding of the mechanism of their connection to related diseases. Although electron microscopy provides certain clues, very little work exists on living cells. The soft x-ray laser method and apparatus described herein is helpful in seeing what is also seen by fluorescence to the ultrastructure itself.

(c) Fluorescent studies of living cells have disclosed a possible connection between the microstructure (cytoskeleton) of a living cell and its detoxification apparatus. When exposed to fluorescent toxic xenobiotics a network of fluorescent emission appears almost immediately along the sites of action and myosin networks of filaments and/or microtubular. X-ray microscopy can shed light on the nature of this process which appears to be connected with cell detoxification. The dependence of this process on the presence of drugs and on metabolic rates as modified by cell injection of substrates may distinguish between the sickness and health of a cell as characterized by its detoxification ability.

(d) In addition to the cytostructure procedure mentioned above, soft x-rays may also disclose the nature of detoxification of other organs too small to be seen clearly by conventional optical microscopy. These include the Gogli apparatus, lysozomos, and the endoplasmic reticulum. These roles have been already hinted at by fluorescence, but x-rays should provide a much clearer picture. Apparently, the vital detoxification process includes the activities of all three organs, and perhaps more.

(e) Many of the processes mentioned above are effected by the metabolic rates of the cell. These rates can be changed at will be microinjection of the substrate followed by monitoring of fluorescence. At the same time and in the same cell, the microstructure can then be observed by soft x-ray microscopy as described above. A comparison can then be made of all the cell processes utilizing the knowledge of the metabolic rate as disclosed by fluorescence.

While the invention has been described with reference to the preferred embodiment thereof, it will be appreciated by those of ordinary skill in the art that modification can be made to the structure and method of the invention without departing from the spirit and scope of the invention as a whole.

We claim:

1. An x-ray laser microscope apparatus for examining a target comprising:
    a source of x-rays in the range of 1 Angstrom to 250 Angstroms for irradiation said target;
    means for supporting said target;
    developable means sensitive to said x-rays for providing an image of said target, said developable means including a resist material which is substantially transparent to human detectable light; and,
    optical means comprising an optical microscope for inspecting said target and aligning said target with respect to said x-rays.

2. The apparatus of claim 1 wherein said optical microscope is located on the opposite side of said transparent resist material from said source of x-rays.

3. The apparatus of claim 2 wherein said optical microscope comprises a Leitz Diavert type microscope.

4. The apparatus of claim 3 wherein said apparatus further comprises:
    a source of red light for illuminating said target;
    mirror means for reflecting said red light onto said target; and,
    Fresnel lens means for focusing said red light from said mirror means onto said target.

5. The apparatus of claim 4 further comprising:
    ultraviolet light source means for illuminating said transparent resist material on the side opposite from said source of red light.

6. The apparatus of claim 5 wherein said source of x-rays comprises a synchrotron source.

7. The apparatus of claim 5 wherein said source of x-rays comprises an x-ray laser.

8. The method of exposing a target to a soft x-ray beam, said method comprising the steps of:
    placing said target on a piece of optically transparent resist material having a first and a second side;
    observing said target from said first side and aligning said target with respect to the anticipated path of said soft x-ray beam; and,
    exposing said target to said soft x-ray beam from said second side.

9. The method of claim 8 further comprising said step of:
    developing said transparent resist material to form an image of said target.

10. The method of claim 9 further comprising the steps of:
    exposing said target to ultraviolet light from said first side; and,
    observing the effects of said ultraviolet light on said target from said first side.

11. The method of claim 10 further comprising the steps of:
    exposing said target to red light from said second side; and,
    observing the effects of said red light on said target from said first side.

12. The method of claim 11 further comprising the step of: injecting material into said target from said second side.

13. The method of claim 12 further comprising the step producing said soft x-ray beam from an x-ray laser.

14. The method of claim 12 further comprising the step of:
    producing said soft x-ray beam from a synchrotron.

15. An x-ray laser microscope apparatus for examining a target comprising:
    a source of x-rays for irradiating said target;
    means for supporting said target;
    transparent resist material which is substantially transparent to human detectable light and sensitive to said x-rays; and,
    an optical microscope for observing said target,
    wherein said optical microscope is located on the opposite side of said transparent resist material from said source of x-rays and wherein said x-rays produce an image of said target on said transparent resist material.

* * * * *